(12) United States Patent
Lamba-Kohli

(10) Patent No.: US 8,790,672 B2
(45) Date of Patent: Jul. 29, 2014

(54) GENERATION OF ANTIMICROBIAL SURFACES USING DENDRIMER BIOCIDES

(76) Inventor: Nina M. Lamba-Kohli, Joppa, MD (US)

( * ) Notice: Subject to any disclaimer, the term of this patent is extended or adjusted under 35 U.S.C. 154(b) by 2035 days.

(21) Appl. No.: 11/357,257

(22) Filed: Feb. 17, 2006

(65) Prior Publication Data

US 2006/0188537 A1     Aug. 24, 2006

Related U.S. Application Data

(60) Provisional application No. 60/654,833, filed on Feb. 22, 2005.

(51) Int. Cl.
*A01N 25/00* (2006.01)
*C07F 7/04* (2006.01)

(52) U.S. Cl.
USPC ............................ 424/405; 424/402; 556/413

(58) Field of Classification Search
USPC ................. 424/402; 210/198.1, 206; 252/175
See application file for complete search history.

(56) References Cited

U.S. PATENT DOCUMENTS

| | | | |
|---|---|---|---|
| 6,017,561 A | 1/2000 | Zhou et al. | |
| 6,242,526 B1 | 6/2001 | Siddiqui et al. | |
| 6,399,688 B1* | 6/2002 | Iida | 524/430 |
| 6,440,405 B1* | 8/2002 | Cooper et al. | 424/78.17 |
| 6,464,971 B1 | 10/2002 | Matthews et al. | |
| 6,482,392 B1 | 11/2002 | Zhou et al. | |
| 6,492,445 B2 | 12/2002 | Siddiqui et al. | |
| 6,559,116 B1 | 5/2003 | Godfroid et al. | |
| 2002/0022012 A1 | 2/2002 | Cooper | |
| 2002/0028753 A1 | 3/2002 | Fischer | |
| 2002/0041862 A1 | 4/2002 | Prusiner et al. | |
| 2003/0082133 A1 | 5/2003 | Cooper | |
| 2003/0135195 A1 | 7/2003 | Jimenez et al. | |
| 2003/0143335 A1 | 7/2003 | Quie et al. | |
| 2004/0033269 A1 | 2/2004 | Hei et al. | |
| 2004/0116320 A1 | 6/2004 | Bettiol | |
| 2004/0135967 A1 | 7/2004 | Carney et al. | |
| 2004/0188359 A1 | 9/2004 | King et al. | |
| 2004/0203075 A1 | 10/2004 | Chudzik | |
| 2004/0251188 A1* | 12/2004 | Skinner et al. | 210/198.2 |

OTHER PUBLICATIONS

Witucki, G. L., "A Silane Primer: Chemistry and Applications of Alkoxy Silanes", A Journal of Coatings Technology, Presented at the 57th Annual Meeting of the Federation of Societies for Coatings Technology, Oct. 21, 1992, Chicago, IL., Dow Corning Coporation, p. 1-4.*

Janiszewska et al. "Low molecular mass peptide dendrimers that express antimicrobial properties"; Bioorg Med Chem Lett. 3(21):3711-3, Nov. 2003.

* cited by examiner

*Primary Examiner* — Tracy Vivlemore
*Assistant Examiner* — Monica Shin
(74) *Attorney, Agent, or Firm* — Ober, Kaler, Grimes & Shriver; Royal W. Craig

(57) ABSTRACT

A silane-QAC-dendritic polymer biocide surface treatment for bath, screen or spray-on application. The silane-QAC-dendritic polymer biocide generally comprises a hyperbranched polymer modified to include functionalized quaternary ammonium for biocidal activity, and further modified to include a functionalized silane moiety to covalently attach the polymer biocide to a variety of substrates through hydrolysis. The hyperbranched polymer may be any one from among a group consisting of dendrimers, dendritic polymers, and hyperbranched polymers, and the functionalized silane moiety may be Siloxane (—Si(OR)3). The resulting surface treatment combines the demonstrated high potency of quaternary ammonium compound dendrimers and hyperbranched polymers with the well-established coupling chemistry of silane functional groups. Upon hydrolysis, the silane groups will covalently attach to functional groups such as amines and hydroxyl groups. This provides an effective biocidal surface treatment for any substrates having exposed hydroxyl, amine or other suitable reactive groups.

15 Claims, 1 Drawing Sheet

GENERATION OF ANTIMICROBIAL SURFACES USING DENDRIMER BIOCIDES

CROSS-REFERENCE TO RELATED APPLICATION(S)

The present application derives priority from U.S. provisional application No. 60/654,833 filed Feb. 22, 2005.

BACKGROUND OF THE INVENTION

1. Field of the Invention

The present invention relates to antimicrobial protection and, more particularly, to a quaternary ammonium anti-microbial finish incorporating dendrimer polymers applied as a thin film coating using a silane coupling agent, and methods of use therefore.

2. Description of the Background

The attachment and subsequent proliferation of microbes at surfaces often results in a number of undesirable health, engineering or aesthetic consequences. For example, water quality may be compromised by the establishment of biofilms in water lines and cooling systems; the attachment of bacteria to medical equipment and textiles contributes to the transmission of infections; the growth of mildew on textiles leads to odors and spoilage. Biofilms are matrix-enclosed bacterial populations adherent to surfaces or interfaces.

Consequently, there has been significant research into methods to attach anti-microbials to useful articles to provide localized, continuous antimicrobial activity at the surface, and overcome the problems associated with microbial colonization. Some antimicrobial agents that are currently used to control environmental colonization may be constrained by their mode of action, or their efficacy. For example, many antibiotics, organic compounds and biocidal metals have been successfully incorporated into engineering materials and woven into fabrics. Because many of these agents act intra-cellularly, the active agent must migrate from the matrix into the microorganism in order to be effective. This may also result in a broader environmental contamination by the active agent. Other approaches include the use of compounds that can release small quantities of chlorine. However, these systems must be periodically recharged using specific wash procedures, which is not practical for many applications. The level of cellular killing is also an important consideration. Biocides are compounds that kill microorganisms such as bacteria, viruses and molds. Many of the current approaches have limited activity against Gram negative bacteria in particular, and may thus be considered "biostats" rather than biocides. The difference is more than just semantic, but can be quantified in terms of log reductions in microbials and survivability (i.e. recovery in the presence of nutrients). Biostatic agents may merely inhibit microbial proliferation, and their limited efficacy means that a significant proportion of cells remain viable, which can then be transferred to other surroundings.

What is desirable is a localized biocidal action that does not migrate from a matrix, and which does not require regeneration. This could improve the performance and lifetime of manufactured items and provide a means to prevent cross-contamination, achieve infection control, and prevent biofilm formation.

Many of the current approaches have limited activity against Gram negative bacteria in particular, and may thus be considered biostats rather than biocides.

Quaternary ammonium compounds (QACs) are a well-known example of an antimicrobial compound and are currently widely used as disinfectants. They are surface-active, wide-spectrum antimicrobial agents in which nitrogen is surrounded by four alkyl groups forming a positively charged molecule. The antimicrobial activity of QACs is markedly improved if a large aliphatic residue is attached to the quaternary nitrogen atom. This cation forms a salt with halogens such as chlorine, bromine or iodine. The biocidal action for QACs relies on an alteration of cell permeability which results in cytolytic damage and subsequent cell death. QACs are effective against a range of microorganisms that includes bacteria, viruses, molds, fungi and yeasts.

It is well-known that dendritic polymers ("dendrimers") can be used as thin film coatings. Dendrimers are well defined, highly branched macromolecules that emanate from a central core. First developed by chemist Donald A. Tomalia and coworkers at Dow Chemical between 1979 and 1980, dendritic architecture brings a very high number of functional groups in a compact space. Subsequent research into dendrimers has endeavored to protect surfaces from soils, stains, ice, graffiti, insects, oils, corrosion and chemical and biological contaminants. For example, R. Mezzenga et al. (Compos. Sci. Technol. (2001), 612 (5), pp. 787-795) describes the use of dendritic polymers as modifiers for epoxy resins. A growing community of researchers is exploring or developing a variety of uses for dendritic macromolecules. These include nanoscale catalysts and reaction vessels, micelle mimics, magnetic resonance imaging agents, immunodiagnostics, agents for delivering drugs or genes into cells, chemical sensors, information-processing materials, high-performance polymers, adhesives and coatings, separation media, and molecular antennae for absorbing light energy and funneling it to a central core (as occurs in photosynthetic systems).

The potential of dendrimers as hosts for other molecules was demonstrated in 1994 by E. W. (Bert) Meijer, chemistry professor at Eindhoven University of Technology in the Netherlands, and his coworkers Johan F. G. A. Jansen (then a postdoctoral associate at Eindhoven) and Ellen M. M. de Brabander-van den Berg, a chemist at DSM Research in Geleen, the Netherlands. They described a "dendritic box" about 5 nm in diameter that can trap smaller molecules in the box's internal cavities [Science, 266, 1226 (1994)].

Dendrimers have also been used to deliver antimicrobials. For example, Balogh et al. synthesized dendrimer nanocomposites, dendrimers with inorganic silver or silver ions, and tested their antibacterial properties. Balogh, L. Proc. Am. Chem. Soc. Div. Colloi. & Surf. Chem., 54. (1999). For these dendrimer nanocomposites, the dendrimer itself did not have any antibacterial property.

U.S. Pat. No. 6,440,405 to Cooper et al. issued Aug. 27, 2002, describes quaternary ammonium functionalized dendrimers suitable for controlling the growth of microorganisms. A quaternary ammonium functionalized dendrimer can be represented by $D_n\text{-}(W)_z$ wherein the chemical structure of the chemical group W of a dendrimer of Generation n, is terminated by a quaternary ammonium compound. Unlike Balogh, Cooper et al.'s quaternary ammonium functionalized dendrimers derive antibacterial properties from the dendrimer itself (the surface groups of the dendrimers were transformed into quaternary ammonium groups). The quaternary ammonium functionalized dendrimers are much more effective against Gram-negative bacteria such as *E. coli* than comparable amounts of quaternary ammonium salt. Chen successfully immobilized these antimicrobial dendrimers onto a polyurethane in solution (post-polymerization) to create non-leaching biocidal polymers (Chen, Z. C. Ph.D. Thesis, 2000, University of Delaware).

Unfortunately, there are many non-polyurethane surfaces that are not as well suited for solution-phase immobilization, for example glass, metal, fabrics and other substrates. It would be greatly advantageous to provide a way to covalently attach quaternary ammonium dendrimer biocides to a wide variety of substrates. Silane is a known coupling agent, but there is the potential for cross-reactions between the silane functionality and the amine groups in the backbone of polypropyleneimine (PPI) dendrimers as shown in Cooper et al. Thus, even if a silane-QAC-dendrimer could be isolated, the potential for cross-linking may result in a limited shelf life.

The present invention avoids this problem by derivatizing polyester-based hyperbranched (dendritic) polymers to attach both quaternary ammonium compounds (quats) and a hydrolysable silane moiety. The quaternary ammonium provides biocidal activity, while the silane moiety provides a means to covalently attach the biocide to a variety of substrates through hydrolysis. The result is a surface treatment that combines the demonstrated high potency of quaternary ammonium compound dendrimers and hyperbranched polymers with the well-established coupling chemistry of silane functional groups. Upon hydrolysis, ethoxysilane groups will couple to functional groups such as amines and hydroxyl groups, and covalently attach. Silane coupling agents are used as surface modifiers to improve the compatibility between glass or any other substrates having exposed hydroxyl groups, and the surrounding matrix in glass fiber composites. Adhesion between the silane modified substrate and the matrix material is greatly improved, and is reflected in superior physical properties. Thus, glass and other substrates such as cotton that have exposed hydroxyl groups, or other reactive groups including amines, can be treated with silane-QAC-hyperbranched polymers to permanently attach biocides to the surface, and make them resist growth of microorganisms, in textiles, filters, clothing, shelters etc. The present invention is an attempt to provide non-leaching biocides that do not require recharging, and that have superior biocidal activity over traditional bacteriostatic linear quat salts.

SUMMARY OF THE INVENTION

Accordingly, it is an object of the present invention to provide a silane-QAC-hyperbranched polymer biocide coating in which high localized concentrations of quaternary ammonium compounds provides biocidal activity, while a silane moiety provides a means to covalently attach the biocide to a variety of substrates through hydrolysis.

It is another object to provide a quaternary ammonium dendrimer biocide capable of covalent attachment to a wide variety of non-polyurethane surfaces, including those that are not well suited for solution-phase immobilization, for example glass, metal, fabrics and other substrates, as well as polyurethane.

According to the above-described objects, the present invention provides a silane-QAC-hyperbranched polymer biocide surface treatment for bath, screen, or spray-on application. The silane-QAC-hyperbranched polymer biocide generally comprises a hyperbranched polymer modified to include functionalized quaternary ammonium for biocidal activity, and further modified to include a functionalized silane moiety to covalently attach the polymer biocide to a variety of substrates through hydrolysis. The hyperbranched polymer may be any one from among a group consisting of dendrimers, dendritic polymers, and hyperbranched polymers, and the functionalized silane moiety may be Siloxane (—Si(OR)3). The resulting surface treatment combines the demonstrated high potency of quaternary ammonium compound dendrimers and hyperbranched polymers with the well-established coupling chemistry of silane functional groups. Upon hydrolysis, methoxysilane and ethoxysilane groups will couple to functional groups such as amines and hydroxyl groups, and covalently attach. A method of formulation is also disclosed. This approach provides an effective biocidal surface treatment for any substrates having exposed hydroxyl and/or amine groups and/or carbonyl groups.

Additional objectives, features and advantages will be apparent in the written description which follows.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENT

Figure 2:
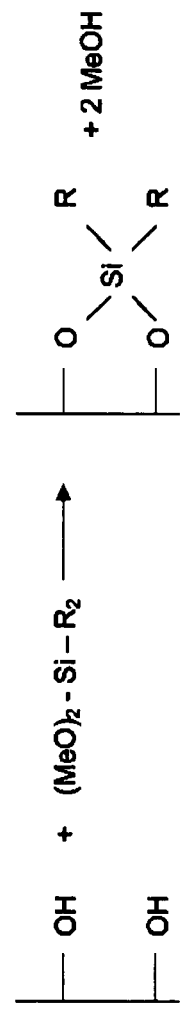
FIG. 2 shows the Bioluminescence of $2*10^9$ cfu/ml $E.$ $coli$ in contact with polyurethane grafted with $3^{rd}$ generation PPI dendrimer containing C12 QAC (Cl— counteranion) (0.1% urethane substitution) (Chen and Cooper, Biomaterials, (2002) vol 23:3359-68).

The present invention is a silane-QAC-dendritic polymer biocide coating in which quaternary ammonium compounds provide biocidal activity, while a silane moiety provides a means to covalently attach the biocide to a variety of substrates through hydrolysis. The invention is intended as a post-fabrication surface treatment by which antimicrobial agents are covalently bonded to various products, textiles, and fabrics for use in various applications (to be described) where antimicrobial properties are advantageous. The antimicrobial agents are based on dendrimers that have been modified to immobilize quaternary ammonium compounds (quats, QACs) at the chain ends. Quats are broad spectrum antimicrobial compounds, and demonstrate very large improvements in effectiveness when present in high local concentrations such as those achieved by immobilization to dendrimers and dendritic and hyperbranched polymers. The present invention yields QAC-Ds, i.e. dendrimers and other highly branched, high molecular weight polymers that have been modified to attach quaternary ammonium compounds at the outer boundary of the molecule. The resulting high local concentrations of quats account for the superior microbicidal properties of these compounds. Moreover, substrate binding is achieved by silane coupling agents. Organofunctional silanes with a typical chemical structure of X—$(CH_2)_n$—Si$(OR)_3$ are the presently-preferred coupling agents. These silanes excel in binding to glass, glass-fiber composites, wood, paper, leather, and synthetic fabrics etc. By incorporating a functional silane group onto the present dendrimer, the net result is a silane-QAC-hyperbranched polymer that can be used as a finishing treatment for a wide range of articles and finished goods to provide biocidal properties in a variety of performance, industrial or medical settings. The silane-QAC-dendritic polymer finishing treatment offers distinct advantages compared with competing technologies in that activity is biocidal rather than biostatic, and since cell death is achieved by membrane disruption, they retain effectiveness when bound to a substrate and can also be non-leaching. The invention can also be used to treat other finished articles including filters, garments, woven and non-woven fabrics, pipes, storage vessels and medical devices for the control of microbial proliferation. The basic components and method of formulation will now be described.

1. Dendrimers, Dendritic Polymers and Hyperbranched Polymers

The present invention makes use of any of the group of dendrimers, dendritic polymers (DP) and hyperbranched polymers (HPB). These are all generally characterized as highly branched 3-D macromolecules that emanate from a central core.

All dendritic structures inclusive of dendrimers, dendritic polymers; and hyperbranched polymer (having lower symmetry), all reflect a compact structure and a large number of reactive end groups that offer the potential to achieve high levels of potency and local concentration. Suitable dendrimers (a) are commercially produced by Dendritech Inc. (Midland, Mich.) and DSM (Geleen, Netherlands) and can be purchased from Sigma-Aldrich (WI). Dendritic polymers are also three-dimensional structures, and can be considered as structurally imperfect dendrimers. Hyperbranched polymers (HPB) also possess significant branching, but lack symmetry. These are also produced commercially, primarily for use as cross-linkers in polymers systems. The Boltorn series of dendritic polymers produced by Perstorp Polyols, Toledo, Ohio is well-suited. Boltorn is a polyester based dendritic molecule, with terminal hydroxyl groups. These structures can be produced more easily in commercial quantities, and hence are much less expensive. The present invention contemplates using any of the foregoing highly-branched 3-D macromolecules that emanate from a central core. This may be any from the group consisting essentially of polyamidoamine, polylysine based dendrimers, polyethylene oxide based dendrimers, silicon based dendrimers, polypropylene imine dendrimers, polyether dendrimers, polyethylene oxide based hyperbranched polymers, polyglycerol based hyperbranched polymers, silicon based hyperbranched polymers, hyperbranched polyols and Hybrane™ from DSM (Geleen, Netherlands).

2. Modification to Attach Quaternary Ammonium Compounds at the Outer Boundary of the Molecule: QAC-Ds The present invention modifies the foregoing general dendrimer and hyperbranched polymer formula to immobilize quaternary ammonium compounds (quats, QACs) at the chain ends (at the outer boundary of the molecule), as follows:

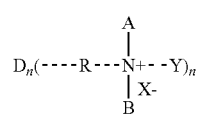

Where D is a dendrimer (any from the above group), n is the number of reactive terminal groups on the unmodified dendrimer or dendritic polymer; X is an anion; R is a linking group; Y is an alkyl group or aryl group; A is an alkyl group or aryl group, and B is an alkyl group or aryl group.

3. Modification of QAC-D to Incorporate Silane Coupling Agents

In addition to the quaternary ammonium compounds, substrate binding is achieved by particular silane coupling agents. Organofunctional silanes with a typical chemical structure of $X-(CH_2)_n-Si(OR)_3$ are the presently-preferred coupling agents as shown.

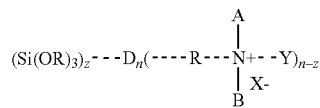

where z is an integer less than or equal to n/10.

4. Method of Formulation of Silane-QAC-Hyperbranched Polymer

The method of composing antimicrobial agents of the present invention in which high molecular weight polymers are modified to attach quaternary ammonium compounds at the outer boundary of the molecule include two steps: 1) Synthesis of Quaternary ammonium compounds (QACs, quats) into QAC-dendrimers, followed by 2) inclusion of silane reactive end group for post-fabrication coupling. The method steps are detailed as follows:

Step 1: Synthesis of Quaternary Ammonium Compounds (QACs, Quats) into QAC-Dendrimers.

This step essentially comprises the substeps of a) halogenation of the terminal amine groups, followed by b) quaternization with a tertiary amine.

These sub-steps are detailed as follows:

a. Halogenation is achieved through reaction with 2-chloroethylisocyanate. The isocyanate group reacts with the terminal hydroxyl groups on the hyperbranched polymer, to produce chlorinated chain ends. For example, 3-5 grams of Perstorp Dendritic polymer Boltorn H40 are dissolved in 100 ml anhydrous DMAc. A total of 60 ml of anhydrous toluene is divided equally into 3 portions and is used to strip moisture in the dendrimer or hyperbranched polymer solution using a rotary evaporator. Because isocyanate chemistry is moisture sensitive, stripping is repeated three or more times. An amount of the isocyanate (3-8 grams of 2-chloroethyl isocyanate, or 2-bromoethyl isocyanate) equivalent to the majority of the available reactive end groups is dissolved in a minimal amount of anhydrous DMAc (ca. 5 ml) and added dropwise to the solution at room temperature. The solution is stirred overnight at room temperature. The isocyanate group reacts with the terminal hydroxyl groups on the dendritic polymer, to produce chlorinated chain ends. The reaction between hydroxyl groups and isocyanates can be catalyzed by selected tin compounds and can be used to promote complete reaction. Gentle heating may also be applied to the reaction vessel to promote reaction. The majority of hydroxyl groups are reacted, leaving some free hydroxyl groups for subsequent silanization (described below).

b. Quaternization with a tertiary amine occurs next. The chlorinated ends of the hyperbranched polymer are then quaternized with stoichiometric amounts of a tertiary amine, such as N,N dimethyloctylamine to generate the quaternary ammonium compounds at the chain ends. The solution is slowly brought up to 80 degrees C. and is stirred for at least 72 hours. Quaternization of the halogenated chain ends is the desired end point.

Quaternary ammonium compounds are usually synthesized by the addition of an alkyl halide to a tertiary amine. It has been shown that quaternary ammonium salts are most effective when one constituent is an alkyl chain with at least eight carbon atoms. Rahn, O.; Van Wseltine, W. Annual Review of Microbiology 1947, 1, 173. The issue of alkyl chain length was considered again when Cutler et al. studied how size affects the antimicrobial activity of a homologous series of alkyldimethylbenzyl ammonium chlorides. They found out that the highest potency is achieved when the alkyl chain has 14 carbons. Block, S. Disinfection, Sterilization and Preservation; 3rd ed.; Lea & Febiger: Philadelphia (1983).

Step 2: Synthesis of QAC-dendrimer with Silane Reactive End Group for Substrate Coupling.

Figure 1:
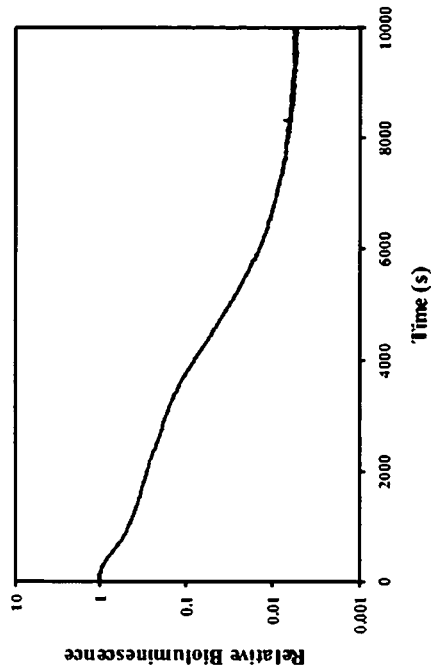
FIG. 1 illustrates the products of the reaction between the quaternized hyperbranched polymer and 3-isocyanatopropyltriethoxysilane.

Organofunctional silanes with a typical chemical structure of X—$(CH2)_n$—$Si(OR)_3$ are suitable coupling agents. By incorporating a functional silane group onto the dendrimer, QAC-dendrimers and hyperbranched polymers can be used as a finishing treatment for textiles to provide biocidal properties for use in a variety of settings. In order to attach silane groups, the quaternized hyperbranched polymer formed as above is reacted overnight with a slight excess compared to the unreacted terminal hydroxyl groups of 3-isocyanatopropyltriethoxysilane as shown by the reaction of FIG. 1. The large excluded volume of the silane group helps to ensure that the isocyanate group is the one that is presented to the unreacted hydroxyl groups on the hyperbranched polymer, and should prevent condensation between unreacted hydroxyl groups on the hyperbranched polymer and the silane from occurring. This also contributes to the stability of the compound in storage.

Figure 3:
FIG. 3 illustrates the reaction of the siloxy groups condensing with each other to produce a cross-linked matrix at the surface.

Siloxane (—$Si(OR)_3$) groups hydrolyze in the presence of moisture, a reaction that is catalyzed by acids, and will condense onto the surface, and will react with hydroxyl groups, amines, carbonyls, etc., to form a covalent bond with the substrate. Depending on functionality and steric constraints, the siloxy groups may condense with each other to produce a cross-linked matrix at the surface, as shown in FIG. 3. A covalent bond is formed as a result of the hydrolysis of the methoxy or ethoxy group, (methanol or ethanol is liberated) linking the desired organic group to the substrate.

The length of the silane compound should be similar to, or slightly exceed the length of the alkylating chain to ensure that the silane group is unhindered for subsequent coupling reactions. A $C_8$ chain is close to the length of the isocyanate-silane, so should minimize the steric hindrance of the silane group when it is being coupled to test surfaces. It is practice to remove moisture in all solvents and reagents when preparing QAC-dendrimers and hyperbranched polymers, and to keep all the reagents dry to avoid side reactions with isocyanates. The absence of water will also prevent hydrolysis of the silane group during preparation of the siloxy/QAC dendrimer moiety. To help achieve uniform distribution, dilution of reagents and vigorous stirring should be used during all steps of synthesis. It has been found that no gelation or precipitation occurred when using the hyperbranched polymers in this reaction scheme, suggesting that cross-linking was not a competing side reaction.

The siloxy/QAC dendrimer is precipitated in hexane and dried by rotary evaporation. A semi-continuous process called diafiltration, a combination of dialysis and ultrafiltration, can be used for further purification. The diafiltration usually takes 2-3 days. The diafiltration may be stopped when the exit stream does not contain any tertiary amine or other small molecules detectable by a gas chromatography-mass spectrometer (GC-MS). Initial characterization of the isolated product using Fourier Transform Infrared Spectroscopy (FTIR) indicates the presence of silanes on the QAC-HPBs. Again, although QAC dendrimers have shown superior biocidal properties to QAC-hyperbranched polymers in the limited number of previous studies that have been performed, hyperbranched polymers are more economical and are also well suited for present purposes. Methyl and ethyl siloxy groups, as well as chlorosilane groups are quite reactive, and there is the potential for cross-reactions between the silane functionality and the amine groups present in polypropylene-imine dendrimers. PAMAM dendrimers have a different backbone chemistry, but are more expensive. Polyester groups on the backbone of the dendritic polymer are not expected to cross react with the silane coupling agent during preparation or surface treatment.

5. Application: Coupling of Silanes to Surfaces Through Hydrolysis

Siloxane (—$Si(OR)3$) groups hydrolyze in the presence of moisture and condense onto the surface, and will react with hydroxyl groups, amines, carbonyls etc. to form a covalent bond with the substrate. Depending on functionality and steric constraints, the siloxy groups may condense with each other to produce a cross-linked matrix at the surface (see FIG. 1). A covalent bond is formed as a result of the hydrolysis of the methoxy or ethoxy group, (methanol or ethanol is liberated) linking the desired organic group to the substrate. Initial application of the QAC-hyperbranched polymers may be by incubating in a bath, by screen application, or by atomized or aerosol spray. Examples are as follows:

Example 1

Coupling to Glass

Glass microscope slides were treated with the new compounds to verify that the compounds can in fact be coupled to glass surfaces. Silanes were deposited from a dilute solution of alcohol (e.g. 1% of reagent in 50/50 water/methanol). A drop of sulfuric acid was added as a catalyst. Hydrolysis occurs, forming a covalent bond between the siloxy group and surface hydroxyl groups, in this case with the elimination of ethanol. Curing of the surface by exposure to heat follows, for example, the treated slides are cured at 80 degrees C. for 24 hours. Successful coupling of the silane resulted in a more hydrophobic surface, causing water to bead up at the surface. The presence of quats at the surface was demonstrated by staining with bromophenol blue solution. Briefly, a 0.02% solution of bromophenol blue in distilled water was prepared and left on the surface of treated and untreated microscopes slides. A few drops of the purple solution was placed on each surface for 2-3 minutes and then each surface was rinsed with distilled water. The treated surface was stained blue, due to retention of the dye, whereas the untreated glass slide remained colorless. The foregoing demonstrates that QAC-dendritic polymers can be immobilized to a glass substrate, via silane coupling. The synthesis of the multifunctional QAC-silane compounds can be further optimized through reagent selection and reaction conditions. For example, if a higher kill rate is desired, this can be accomplished by increasing the length of the alkyl chain of the siloxy raw material.

Example 2

Coupling to Cotton

Cotton is a cellulosic fiber. The primary and secondary hydroxyl groups in cotton, as well as the β-glycosidic ether linkages play a significant role in determining the fiber's chemical and physical properties. Several cellulose chains are held together by hydrogen bonds in close alignment to form crystalline microfibrils. The microfibrils in turn align themselves into larger organizational units, or fibrils. These fibrils are usually laid down in a helical fashion. Void and amorphous (unordered) regions exist between crystalline regions. Untreated cotton is thought to be about 70% crystalline. In processing raw cotton into a finished garment, the fiber is subjected to a number of chemical and physical processes. Mercerization of cotton refers to the treatment of cotton with a caustic solution (typically 15-25% sodium hydroxide) to induce a diametric swelling of the fiber, associated with longitudinal shrinkage. If the fabric is held under tension while being treated, shrinkage is controlled, and a high luster on the fabric is produced. Mercerization is irreversible, and reduces the degree of crystallinity of cotton from 70% to about 50%. The size of crystallites is also reduced. Of greater importance is the observed increase in absorption of moisture and dyes into the fibers following the mercerization process. This is believed to arise from the increased number and availability of hydroxyl groups in the amorphous regions that are available for chemical reaction or cross-linking. These cellulosic OH groups will undergo chemical reactions typical of other hydroxyl groups and have been used in cross-linking reactions when applying finishes to cottons, or applying dyes including reactive dyes.

Coupling to Other Substrates

The foregoing coupling of the QAC-silane compounds can be applied to broad range of substrates, and particularly any substrates having exposed hydroxyl and/or amine groups such as fabric and flooring, glass, polyester, polyamides, polyalcohols, plastic, ceramic and cotton. Thus, the invention can also be used to treat a variety of finished articles including air and water filters, garments, woven and non-woven fabrics, glass screens, ductwork, pipes, storage vessels, computer keyboards, instrument panels and medical devices for the control of microbial proliferation. One skilled in the art will understand that the present coupling method is not intended to be limited solely to amine or hydroxyl surfaces, and may be effective on other surfaces as well.

6. The End Product

Biocidal activity has been demonstrated against Gram-positive and Gram-negative bacteria. Furthermore, bacteria do not recover when they are transferred to a less hostile environment or a food source. Modifying articles to immobilize membrane disrupting biocides at the surface provides a unique combination of high antimicrobial performance that does not release the biocide into the broader environment, and does not require periodic recharging (as some chlorine releasing treatments do).

Moreover, it can be applied to a wide range of surfaces for microbial protection. The applications range amongst the following industries: textile finishing (e.g. clothing), carpets, flooring, household finishing, bedding, touch-screens (e.g. screens used to place food orders at restaurants and automated teller machines), medical textiles (e.g. wound dressings), medical devices, air filters, and water tanks (to prevent biofilm/slime development), plastics and polymers (for example polyurethanes, polystyrene, rubber, polyethylene, polypropylene, and other engineering plastics). The functionalized silane-QAC-dendrimers are also intended for industrial as well as medical and home use applications including but not limited to elements of protective coatings such as paints, hand-wash formulations, means for use in ointments and related topical applications, cosmetics, cleaning and/or disinfectant/sanitation products, and sanitation of recreational water such as swimming pools and spas. Despite a high level of efficacy against a wide range of microbial agents the dendrimer biocides of the present invention are non-reactive and are virtually nontoxic to human skin. Specific applications follow:

a. High Performance Fabrics

Performance apparel (sports and active wear) represents one of the most dynamic sectors of the international textile and clothing industry. T-shirts incorporating antimicrobial agents are purported to provide odor control through the control of odor generating bacteria. Antimicrobial finishes can also be used to increase the level of protection offered by protective garments. Tents and shelter fabrics are subjected to microbial degradation in use and in storage. Effective, long-lasting biocidal fabric treatments can be applied to prevent mildew formation and odor. It is estimated that the coated fabrics market will be driven by demand in protective clothing, awnings and tents (among others). These fabrics include cotton, polyester and other synthetics. The functionalized silane-QAC-dendrimers of the present invention may be applied to fabrics by bath during the production process, or by spray (aerosol or atomizer) as a post-fabrication treatment. In both cases the silane-QAC-dendrimers are immobilized on the fabric by covalent bonding as cross-linked (cured) networks or as interpenetrating networks.

b. Medical Textiles

Since the number of deaths in the United States due to hospital associated infections has been estimated to exceed 100,000 per year, and those people with infections require an average of 6-7 extra days in the hospital, the need for biocidal protection is clear. Pathogens and antibiotic resistant bacteria can be recovered or transferred from stethoscope covers, privacy curtains, white coats, surgical scrubs, instrument panels and keyboards etc. through direct contact with the items, or via the fingers. Reports in the literature suggest that bacteria preferentially adhere to synthetic fabrics such as polyester when compared with cotton. Many of these items, including polyester privacy curtains, are laundered infrequently, if at all. The use of biostatic agents in hospital laundry rinse cycles may reduce proliferation of adhered bacteria, but not significantly impact their survivability. Viable bacteria can still be transferred and proliferate in more friendly surroundings. Since the present biocidal agent by definition kills the cell, it is the most effective way to minimize cross-contamination. Medical textiles can be classified in three categories: surgical, extracorporeal, and healthcare/hygiene. Further classifications of medical textiles can be made, depending on whether one considers the physical form of the textile (woven, filamentous etc.), or implantability. The functionalized silane-QAC-dendrimers of the present invention can increase the infection control properties of medical textiles, without significantly adding to the weight, or reducing comfort when applied to garments. The functionalized silane-QAC-dendrimers of the present invention may be grafted directly to these and other fabrics on a large scale, using a bath or vat process, or may be applied to only one side of the textile by spray-on. In both cases the treatment will confer biocidal properties to the textile, rather than being merely bacteriostatic. The potential for cross-contamination and transmission of infections from patient to patient, and the health risks to the wearer will be significantly reduced.

c. TFT Displays

The functionalized dendrimers can also be immobilized on the surface of solid materials to create efficient antimicrobial environments in a wide variety of applications including polymers, glass, and metals. One promising application is thin film (TFT) display screens, and especially touch-screen displays, which are normally used by many different people and are seldom if ever cleaned. Touch screens at fast food restaurants are not treated at all today, and yet pose a significant health hazard and liability issue. The functionalized silane-QAC-dendrimers of the present invention create a new application here because they can be applied in a microscopically-thin layer by spray, and remain clear so as not to affect the visibility of the screen. The treatment confers lasting biocidal properties, to prevent the transmission of bacteria amongst users of the TFT through contact with the TFT screen.

d. Other Applications

Other applications include carpets, flooring, household finishing, medical devices, air filters, water tanks (for the prevention of biofilm/slime formation), all molded plastics and polymers (including polyurethanes, polystyrene, rubber, polyethylene, polypropylene, etc.). The functionalized silane-QAC-dendrimers may also be an additive to protective coatings such as paints, handwash formulations, ointments and related topical applications, cosmetics, cleaning and/or disinfectant/sanitation products, and sanitation of recreational water such as swimming pools and spas. The functionalized silane-QAC-dendrimers may also be used to treat disposable apparel such as the garments used to protect personnel during the clean up and decontamination of areas contaminated with hazardous or biological waste.

7. Test Results

To confirm the chemical nature of the isolated product, FTIR spectroscopy has been used to determine the presence of methoxy groups, siloxy groups, and quaternary ammonium groups (key markers for interpretation of spectra) in the isolated product. Nuclear Magnetic Resonance (NMR) could allow a more powerful determination of ratios of silane groups to quaternary ammonium groups, and can be used if further characterization is required. The antibacterial properties of the QAC-terminated dendrimers have been tested using Gram-positive bacteria (*Staphylococcus aureus*), and Gram-negative bacteria (*Escherichia coli*) and were found to be highly toxic against both organisms. When tested in suspension, the toxic effect of the QAC-dendrimer D3ClNC12 a $3^{rd}$ generation PPI dendrimer immobilized with C12 QAC, Cl— counterion against *E. coli* was more than 100 times greater than the effect exerted by a comparable amount of QAC alone. Lower effective concentrations were required to achieve the same kill rate (at approx. 100 ug/ml), and at lower concentrations (25 ug/ml) the QAC dendrimers had a much more marked effect on cell viability (as measured by optical density) than the free quat salt. Solution tests performed using *Pseudomonas aeruginosa* showed susceptibility of the organisms to the QAC dendrimers, whereas the free quat salt was ineffective against the bacteria. Five species of bacteria *Escherichia coli, Salmonella typhimurium, Pseudomonas aeruginosa, Streptococcus pyogenes* and *Staphylococcus aureus* were also tested. *Pseudomonas aeruginosa* was resistant to most of the samples tested, following incubation for 24 hours.

FIG. 2 shows the Bioluminescence of 2*109 cfu/ml *E. coli* in contact with polyurethane grafted with $3^{rd}$ generation PPI dendrimer containing C12 QAC (Cl— counteranion) (0.1% urethane substitution). Data were confirmed by employing traditional plating methods, with wild type bacteria (i.e. not genetically modified). The negative control (unmodified polymer) showed an increase in the number of viable cells with time, implying that cells were able to reproduce. At a level of substitution of 0.1% of the urethane hydrogen (corresponding to 1.5-2.0 wt % of the derivatized third generation dendrimer), the immobilized QAC-dendrimer D3ClNC12 was able to exert a toxic effect on both *S. aureus* and *E. coli*. 99% reduction in *E. coli* was achieved after approx. 2 hours. By comparison, polyurethane derivatized with QAC alone was able to kill *S. aureus* but not *E. coli*. Only a small loss in mechanical properties of the base polymer was observed (Chen and Cooper, Biomaterials, 23 (16): 3359-68).

Studies comparing the efficacy of modified and unmodified polyurethanes were completed. Test organisms (*S. aureus*) were grown overnight in Trypticase Soy Broth (TSB) at 37° C. After incubation they were washed twice in Phosphate Buffered Saline (PBS), diluted and plated on Trypticase Soy Agar (TSA) for cell enumeration. Ten µl aliquots were removed from the appropriate dilutions to yield ~1,000 and 10,000 organisms and applied to coated and uncoated (control) slides. In addition, ten µl aliquots of PBS were applied to test and control slides. The slides were then put into individual Petri plates which were placed in gasketed containers containing water filled beakers to maintain humidity during the two hour incubation period at 37° C. After incubation, 2 µl were removed from each drop and plated onto TSA plates for enumeration. The slides were then inverted onto TSA plates and incubated overnight at 37° C. Growth was scored as + or –. Growth of *S. aureus* was seen on the unmodified polymer (negative control). No growth was observed on the Estane/QAC-dendrimer sample. Growth was inhibited on a polyurethane that was modified to contain linear quaternary ammonium compound moieties (Goddard and Cooper, J. Polymer Sci., Polym. Phys. Ed. 32:1557-1571), although some colonies were established when transferred to the agar medium.

It should now be apparent that the present invention provides a silane-QAC-hyperbranched polymer biocide coating based on polyester based hyperbranched polymers, in which functionalized quaternary ammonium provides biocidal activity, while a silane moiety provides a means to covalently attach the biocide to a variety of substrates through hydrolysis.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth herein.

I claim:

1. A silane-QAC-hyperbranched polymer biocide, comprising a plurality of polyester based hyperbranched dendritic molecules each characterized by a first plurality of chain ends modified by halogenation to produce chlorinated chain ends defined by terminal hydroxyl groups, followed by quaternization with a tertiary amine to include functionalized quaternary ammonium molecules linked as end groups for biocidal activity, and a second plurality of chain ends modified to include a functionalized silane moiety linked as end groups to covalently attach the polymer biocide to a variety of substrates through hydrolysis.

2. The silane-QAC-hyperbranched polymer biocide according to claim 1, wherein said functionalized silane moiety is Siloxane (—Si(OR)3).

3. A biocidal surface treatment for application to a substrate, comprising:
   a quaternary ammonium compound;
   a hydrolysable silane moiety; and
   a derivatized polyester-based dendritic polymer comprising a plurality of dendritic chains modified by halogenation to produce chlorinated chain ends defined by terminal hydroxyl groups, molecules of said quaternary ammonium compound being linked as end groups to a first plurality of the chain ends of said dendritic polymer, leaving terminal hydroxyl groups at a second plurality of chain ends unreacted, and molecules of said hydrolysable silane moiety being linked as end groups to said second plurality of unreacted chain ends of said dendritic polymer;
wherein said quaternary ammonium compound provides biocidal activity and said silane moiety allows covalent attachment of the quaternary ammonium compound to a variety of substrates through hydrolysis.

4. The biocidal surface treatment according to claim 3, wherein said silane moiety prevents leaching of said quaternary ammonium compound.

5. The biocidal surface treatment according to claim 3, wherein said hydrolysable silane moiety will couple to any substrate having exposed hydroxyl and/or amine groups and/or carbonyl groups.

6. The biocidal surface treatment according to claim 5, wherein said substrate includes functional amines and hydroxyl and carbonyl groups, and whereupon hydrolysis of said hydrolysable silane moiety couples to the functional amines and hydroxyl and carbonyl groups of said substrate and covalently attaches thereto.

7. The biocidal surface treatment according to claim 3, wherein said dendritic polymer comprises immobilized quaternary ammonium compounds at an outer molecular boundary.

8. The biocidal surface treatment according to claim 3, wherein said dendritic polymer comprises a plurality of dendrimers having the following formula:

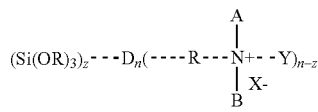

where D is a dendrimer, n is a number of reactive terminal groups, X is an anion, R is a linking group, Y is an alkyl, fluoroalkyl or aryl group, A is an alkyl, fluoroalkyl or aryl group, B is an alkyl, fluoroalkyl or aryl group, and z is an integer less than or equal to n/10.

9. The biocidal surface treatment according to claim 3, wherein said dendritic polymer comprises any hyperbranched polymers from among a group comprising polyamidoamine dendrimers, polylysine based dendrimers, polyethylene oxide based dendrimers, based dendrimers, polypropylene imine dendrimers, polyether dendrimers, fluoroalkyl dendrimers, polyglycerol dendrimers, polyamidoamine hyperbranched polymers, polyethylene oxide based hyperbranched polymers, polylysine hyperbranched polymers, polyethylene oxide hyperbranched polymers, polyglycerol based hyperbranched polymers, silicon based hyperbranched polymers, fluoralkyl hyperbranched polymers, hyperbranched polyols, polyether hyperbranched polymers and Hybrane™.

10. A biocidal surface treatment according to claim 3 adapted for application to said substrate by anyone of incubation therewith in a bath, by screen application thereto, or by atomized or aerosol spraying thereon.

11. A biocidal surface treatment according to claim 3 suitable for immobilization to said substrate by sitane coupling, said substrate being anyone from among the group including glass, fabric, flooring, polyester, polyamides, polyalcohols, plastic, ceramic and cotton.

12. A biocidal surface treatment according to claim 3, wherein said substrate comprises an article of manufacture chosen from among a group comprising air filters, water filters, garments, woven and non-woven fabrics, glass screens, ductwork, pipes, storage vessels, computer keyboards, instrument panels, medical devices, carpets, flooring, bedding, touch-screens, medical textiles, medical devices, water tanks, plastics and polymers.

13. A biocidal surface treatment according to claim 3, further comprising a carrier from among a group comprising paint, hand-wash, topical ointment, cosmetic, cleaning product, disinfectant product, and water purification product.

14. A biocidal surface treatment according to claim 3 that is non-reactive and substantially nontoxic to human skin.

15. A biocide comprising a plurality of hyperbranched polymers each characterized by a plurality of dendritic chains leading to chain ends characterized by terminal hydroxyl groups, a first plurality of said chain ends being halogenated to chlorinate the terminal hydroxyl groups, the chlorinated first plurality of chain ends of said hyperbranched polymers being modified to include functionalized quaternary ammonium molecules linked as end groups for biocidal activity, and an unreacted second plurality of chain ends being modified to include a functionalized silane moiety linked as end groups to covalently attach the hyperbranched polymer, said biocide being covalently attached to any one from among a group including a medical device, a filter impregnated with said biocide, a touch screen display comprising an LCD panel coated with said biocide, and an article of fabric comprising a woven or non-woven fabric impregnated with said biocide.

* * * * *